(12) United States Patent
Kasha et al.

(10) Patent No.: US 6,812,028 B1
(45) Date of Patent: Nov. 2, 2004

(54) EMBRYOGENESIS AND PLANT REGENERATION FROM MICROSPORES

(75) Inventors: Kenneth J. Kasha, Guelph (CA); Ecaterina Simion, Guelph (CA)

(73) Assignee: University of Guelph, Guelph (CA)

( * ) Notice: Subject to any disclaimer, the term of this patent is extended or adjusted under 35 U.S.C. 154(b) by 0 days.

(21) Appl. No.: 09/460,324

(22) Filed: Dec. 10, 1999

(51) Int. Cl.$^7$ ................................................ C12N 5/00
(52) U.S. Cl. .................... 435/430.1; 435/430; 435/420; 435/410; 435/468; 435/469; 435/470; 800/278; 800/293; 800/294; 800/299
(58) Field of Search .............................. 435/430.1, 430, 435/420, 410, 468, 469, 4, 431, 440; 800/278, 293.2, 293, 294

(56) References Cited

U.S. PATENT DOCUMENTS

| | | | |
|---|---|---|---|
| 4,840,906 A | | 6/1989 | Hunter ................... 435/240.49 |
| 5,445,961 A | * | 8/1995 | Genovesi et al. ......... 435/240.5 |
| 5,610,042 A | * | 3/1997 | Chang et al. ............. 435/172.3 |

FOREIGN PATENT DOCUMENTS

| | | | | |
|---|---|---|---|---|
| EP | 0455597 A | * | 4/1991 | ............ C12N/5/00 |
| EP | 0 455 597 A1 | | 4/1991 | ............ C12N/5/00 |
| EP | 0 455 597 | * | 6/1991 | ............ C12N/5/00 |
| WO | WO 89/00602 | | 1/1989 | ............ C12N/15/00 |
| WO | WO 92/14828 | | 9/1992 | ............ C12N/15/84 |
| WO | WO 96/29419 | | 9/1996 | ............ C12N/15/82 |
| WO | WO 00/14202 | | 3/2000 | ............ C12N/5/00 |

OTHER PUBLICATIONS

Hu et al., Plant Cell Reports, (1997), 16:520–525.*
Hu et al., Plant Cell Reports (1997) 16: 520–525.*
Hu et al, In Vitro Cell Dev Biol 31:79–83 (1995).*
Hu, et al., "A cytological study of pretreatments used to improve isolated microspore cultures of wheat (*Triticum aestivum* L.) Cv. Chris," *Genome* 42:432–441 (1999).
Pechan, Paul M., "Successful cocultivation of *Brassica napus* microspores and proembryos with Agrobacterium," *Plant Cell Reports* 8:387–390 (1989).
Rubinstein, et al., "Developmental accumulation of hydroxyproline and hydroxyproline–containing proteins in Zea mays pollen," *Sexual Plant Reproduction* 8:27–32 (1995).
Carlson, Alvar R., "Visual Selection of Transgenic Barley (Hordeum Vulgare L.) Structures and Their Regeneration Into Green Plants," Thesis presented to The Faculty of Graduate Studes of the University of Guelph (Sep. 1998).
Egertsdotter et al., Importance of arabinogalactan proteins for the development of somatic embryos of Norway spruce (*Picea abies*), *Physiologia plantarum* 93:334–345 (1995).
Hu, et al., "Isolated Microspore Culture of Wheat (*Triticum aestivum* L.) in a Defined Media I. Effects of Pretreatment, Isolation Methods, and Hormones," *In Vitro Cell Dev. Biol.* 31:79–83 (1995).
Hu et al., "Improvement of isolated microspore culture of wheat (*Triticum aestivum* L.) through ovary co–culture," *Plant Cell Reports* 16:520–525 (1997).
Jahne, et al., "Regeneration of transgenic, microspore–derived, fertile barley," *Theor. Appl. Genet.* 89:525–533 (1994).

(List continued on next page.)

*Primary Examiner*—Anne Marie Grunberg
(74) *Attorney, Agent, or Firm*—Quarles & Brady LLP

(57) ABSTRACT

A method for embryogenesis and a method for plant regeneration are disclosed. Microspore-containing plant segment from donor plants are harvested and incubated under pre-treatment conditions to maintain microspore at a uninucleate cell cycle G1 phase. Pre-treatment conditions comprise cold water or an aqueous solution of about 0.2–about 1.0 mol/liter sugar alcohol, for example mannitol. Microspores are isolated from the plant segment and embryogenesis of microspores is induced in induction medium, thereby producing embryos. Green plants may be regenerated from the embryos produced. Arabinogalactan protein, auxin and ovary co-culture may be added to the induction medium to enhance embryogenesis from microspores.

27 Claims, 6 Drawing Sheets

OTHER PUBLICATIONS

Kasha, et al., "Use of Haploids in Induced Mutation in Barley and Wheat," *Cereal Research Communications* 19:101–108 (1991).

Kasha et al, "Production and Application of Doubled Haploids in Crops," *International Atomic Energy Agency* pp 23–37 (Jun. 1995).

Kasha et al., "Anther and microspore cultures of barley and wheat," *J. Appl. Genet.* 38:373–380 (1997).

Kawaguchi et al., "A novel tetrasaccharide, with a structure similar to the terminal sequence of an arabinogalactan–protein, accumulates in rice anthers in a stage–specific manner," *The Plant Journal* 9:777–785 (1996).

Kreuger, et al., "Arabinogalactan proteins are essential in somatic embryogenesis of *Daucus carota L.,*" *Planta* 189:243–248 (1993).

Kuhlmann, et al., "Improved Culture System for Microspores of Barley to Become a Target for DNA Uptake," *Plant Breeding* 107:165–168 (1991).

Lettre et al., "Ill.6 Wheat Anther Culture Using Liquid Media," *Biotechnology in Agriculture and Forestry* 13:416–424 (1990).

Roberts–Oehlschlager et al., "Barley anther culture: Pretreatment on mannitol stimulates production of microspore–derived embryos," *Plant Cell, Tissue and Organ Culture* 20:235–240 (1990).

Wheatley et al., "Microspore growth and anther staging in barley anther culture," *Plant Cell Reports* 5:47–49 (1986).

Yao, et al., "Biolistic transformation of haploid isolated microspores of barley (*Hordeum vulgare L.*)," *Genome* 40:570–581 (1997).

Ziauddin, et al., "Improved plant regeenration from shed microspore culture in barley (*Hordeium vulgare L.*) cv. Igri," *Plant Cell Reports* 9:69–72 (1990).

Ziauddin et al., "Imrpoved plant regeneration from wheat anther and barley microspore culture using phenylacetic acid (PAA)," *Plant Cell Reports* 11:489–498 (1992).

\* cited by examiner

US 6,812,028 B1

EMBRYOGENESIS AND PLANT REGENERATION FROM MICROSPORES

The present invention relates to methods for producing embryos and regenerating plants from cultured microspores.

BACKGROUND OF THE INVENTION

Doubled haploid plants can be generated from hapioid plants or cells in which the chromosome number is doubled to the normal somatic number(2n) by duplication. Methods for production of haploid and doubled haploid plants have application to plant breeding and transgenic plant production.

The induction of microspore division leading to embryogenesis has application to large-scale haploid and doubled haploid plant production. Methods are known which induce formation of embryo-Like structures from microspores in which genotypes within a species can be induced to produce large numbers of haploids. However, the regeneration of green plants from such embryos has been problematic using known methodology. Genotypes of some monocotyledonous species such as cereals produce albino plants from embryo-like structures. Conventional isolated microspore culture techniques have not led to consistent embryo regeneration, and disadvantageously result in the production of a high proportion of albino plants.

U.S. Pat. No. 4,840,906 (Hunter) teaches a method of plant regeneration from barley microspores incubated at 25° C. for 28 days in a sugar-containing culture medium following 28 days of cold pre-treatment. The method disclosed results in wide variation in the rate of green plantlet formation from microspores, ranging anywhere from about 30 to about 200 green plantlets formed per 100 anthers cultured. There is clearly a need for an improved method that consistently produces high yields of green plantlets from isolated microspores.

U.S. Pat. No. 5,445,961 (Genovesi et al.) discloses a method for embryogenesis of microspores using a pretreatment of sugar alcohol and cold (about 10° C.) which also requires colchicine, a chromosome doubling agent. This pretreatment is followed by microspore isolation and growth on culture medium. From 2 to 115 embryoids were produced for every $10^4$ microspores incubated according to this method. Transformation of microspores after treatment with a chromosome doubling agent would be less likely to result in homozygous transformants than if transformation were to occur prior to chromosome doubling. However, no transgenic transformation of microspores is disclosed in this document.

The haploid single-celled microspore is an attractive target for mutation, selection, and transformation. When transformation is performed at the G1 phase of the nuclear cycle, genetically homozygous plants are produced which include transgenes introduced prior to division. Yao et al. (*Genome* 1997;40:570–581) treated highly inducible barley microspores of the genotype Igri with mannitol, followed by biolistic bombardment to transform the microspores. However, the regenerated plants were largely heterozygous for the transgene.

Jähne et al. (*Theor Appl. Genet.* 1994;89:525–533) describes a method of using barley isolated microspores for particle bombardment. From cold pretreated spikes, microspores were quickly isolated and maintained at about 24C for 1 hour prior to bombardment with a transgene. An average of 82 green plants per $10^5$ microspores were produced according to the disclosed method, and only one transgenic plant formed for every $2.8 \times 10^6$ microspores.

Methodological conditions which contribute to successful methodology for embryogenesis, and plant regeneration include donor plant growth, pre-treatment, culture medium components, such as sugar type, nitrogen source and balance, hormones, and medium density and osmolality. However, a method resulting in a high rate of embryogenesis, and successful production of high numbers of green plants has not been disclosed. A methodology is required which employs a optimal and synergistic combination of the above-noted conditions, resulting in a high production rate of green plants from microspores. Such an improved method would be labor saving, and of higher efficiency than conventional methodology, thereby reducing production costs.

Arabinogalactan proteins (AGP) are plant proteoglycans present in a diverse number of plant tissues which may have regulatory functions in plant cell reproduction processes. Previous reports have illustrated positive effects of arabinogalactan proteins on somatic embryogenesis in *Picea abies*(Norway Spruce) and in *Daucus carota* L. (see, for example Egertsdoner et al. *Physiol Plant* 1995;93:334–45; and Kreuger et al. *Planta* 1993;189:243–248). Kawaguchi et al. (Plant Journal, 1996;9(6):777–785) describe a tetrasaccharide similar in structure to arabinogalactan protein, which accumulates in rice anthers in a stage-specific manner. The effects of AGP on embryogenesis and plant regeneration from microspores has not been evaluated.

European Patent Publication No. 0 455 597 A1 (Sandoz Ltd) discloses a method for stimulating growth of *Daucus carota L* cells plants in in vitro culture. This publication describes the stimulation of growth by adding AGP to culture medium at a level of from 0.01 to 100 mg/L. However, AGP was not used or assessed for efficacy in inducing embryogenesis of microspores. Additionally, no transformation methodology or staging of cells in culture is taught.

There is a need for a method of embryogenesis which results in the production of green plants with a high success rate.

There is also a need for an effective method of plant transformation from embryogenic induction of microspores, which provides an effective pre-treatment to synchronize microspores and holds them at the G1 phase of the cell cycle prior to transformation, thereby increasing the production of homozygous transformants.

It is an object of the invention to overcome disadvantages of the prior art. The above object is met by the combinations of features of the main claims, the sub-claims disclose further advantageous embodiments of the invention.

SUMMARY OF THE INVENTION

The present invention relates to methods for producing embryos and regenerating plants from cultured microspores.

According to this invention, there is provided a method of embryo production comprising the steps of (a) harvesting a microspore-containing plant segment from a donor plant; (b) incubating the segment under pretreatment conditions to maintain a substantial portion of microspores at a uninucleate cell cycle G1 phase; (c) isolating microspores from the segment; and (d) incubating said isolated microspores in an induction medium comprising arabinogalactan protein to induce embryogenesis, thereby producing embryos.

Further, the invention provides a method of plant regeneration from micro spores comprising the steps of (a) harvesting a micro spore-containing plant segment from a donor plant; (b) incubating the segment under pre-treatment conditions to maintain a substantial portion of microspore uninucleate cell cycle G1 phase; (c) isolating microspores from the segment; (d) incubating the isolated microspores in an induction medium comprising an auxin to induce the production of embryos; (e) incubating the embryos in a differentiation medium to produce differentiated embryos; and (f) regenerating plants from the differentiated embryos.

The present invention is also directed to the production of an embryo that is prepared by the above method, and to a plant produced from this embryo.

This invention pertains to a method of introducing a gene of interest into a microspore comprising introducing a genetic construct comprising the gene of interest into the microspore following the steps of pretreatment and isolation. Methods for introducing the genetic construct into the microspore comprise particle bombardment or Agrobacterium mediated transformation. Furthermore, the present invention is directed to a transgenic microspore prepared by this method, and to a transgenic embryo and transgenic plant produced from this transgenic microspore and transgenic embryo, respectively.

Advantageously, the method is efficient and labor saving as compared with known microspore culture and anther culture procedures. The higher success rate for green plant production according to the inventive method will result in cost savings. A further benefit of the inventive methodology is a reduction in the number of albino plants produced.

Advantageously, the inventive method is effective across genotypes, illustrating the absence of a strong genotype effect. The synergistic combination of factors result in a versatile method which may be applied to many types of plants.

Advantageously, the removal of the anther wall during microspore isolation allows for better nutrient availability to microspores during induction, differentiation and regeneration steps. The use of an the embryo support during regeneration facilitates observation of the embryos placed thereon. The use of a support also promotes growth and facilitates the transfer of embryos to different media or treatments.

The pre-treatment maintains a large population of uniformly staged haploid microspores formed according to the method of the invention provides better targets for mutation, selection and transformation of plants. Using the inventive method, transgenic plants may be formed from microspores following pre-treatment by any conventional transformation method, such as bombardment with a transgene.

A pre-treatment to maintain microspores at a common stage of the cell cycle allows production of large number of embryos and regenerated plants from isolated microspores. The combination of cold plus sugar alcohol during the pre-treatment permits a much shorter treatment duration than using just cold treatment alone. Nearly all genotypes respond to this combined cold and sugar alcohol treatment.

The use of the combined cold plus sugar alcohol pre-treatment not only induces large numbers of embryoids but also tends to synchronize microspore cell divisions, thus leading to a more uniform microspore population. The likelihood of nuclear division during pre-treatment is reduced using the combined cold and sugar alcohol pre-treatment. This could be valuable for methodologies involving microspore transformation, testing expression of gene constructs, in vitro selection, or other microspore uses.

The use of arabinogalactan protein during induction of embryogenesis results in an increased yield of microspore embryos from pre-treated plant segments, thereby enhancing the efficiency of the method for embryogenesis.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 3(a) shows the filtering of microspores through cheesecloth. FIG. 3(b) shows the microspore pellet in the tube after centrifugation. FIG. 3(c) shows the placement of microspores on filter paper by vacuum filtration.

FIG. 4(a) shows embryos at 3 weeks after initiation of cultures on filter paper. FIG. 4(b) shows embryos at 5 weeks after initiation of cultures on filter paper.

FIG. 5(a) shows embryo development in wheat c.v. Bob White at 4 weeks with (left hand plates) and without (right hand plates) ovary co-culture, and in the presence (top plates; 10 mg/L) and absence (bottom plates)of AGP. FIG. 5(b) shows barley embryo development in the presence of 10 mg/L AGP (left hand plate), or the absence of AGP (right hand plate).

FIG. 6(a) embryo development of wheat in culture. FIG. 6(b) isolated embryos.

DESCRIPTION OF PREFERRED EMBODIMENTS

The present invention relates to a method for embryogenesis and a method of plant regeneration from microspore culture. These methods are described herein below in more detail with reference to FIGS. 1 to 5. Examples of cereal plant embryogenesis and regeneration are described in further detail, but the invention is not to be limited to cereal plants.

The following description is of a preferred embodiment by way of example only and without limitation to the combination of features necessary for carrying the invention into effect.

By "microspore-containing plant segment", it is meant any portion of a donor plant which may contain microspores to be isolated. Such segments include but are not considered limited to tillers, spikes, anthers, florets, tassels or pannicles.

By "initial treatment" of microspore-containing plant segments, it is meant those procedures conducted after a segment is harvested, but before pre-treatment. Such procedures as cleaning with alcohol or bleach, and washing or incubations in water, as described herein below are included in initial treatment.

By "pre-treatment", it is meant those procedures conducted on microspore-containing plant segments after initial treatment and prior to placement on, or in, embryogenic induction media. Such procedures include incubation under cold conditions in water, in a high osmotic aqueous sugar alcohol solution, or a combination thereof. Pre-treatment creates conditions which serve to block the microspore cell cycle at the uninucleate cell cycle G1 phase, maintain substantially all microspores at this uninucleate stage of development, and trigger future embryogenic induction. The pre-treatment prepares uninucleate microspores for embryogenic induction by maintaining a synchronized population of microspores having from about 50% to 100% of the microspores at a consistent cell cycle G1 phase.

Three stages independently control haploid plant production from microspores, namely the induction of embryogenesis; the regeneration of embryo-like structures; and development of the embryo-like structures into green plants. To accomplish an effective product, the conditions at each stage must be optimized.

A variety of factors must be controlled for effective production of green homozygous plants from microspore culture. Each factor effects one of the above-noted stages in haploid plant production from microspores. The factors of donor plant growth conditions, harvest of spikes, microspore stagging, pre-treatment, microspore isolation, induction conditions, differentiation conditions, plating of embryos, and plant regeneration conditions are all to be optimized for a successful approach to growth of homozygous plants from microspore culture.

Figure 1:
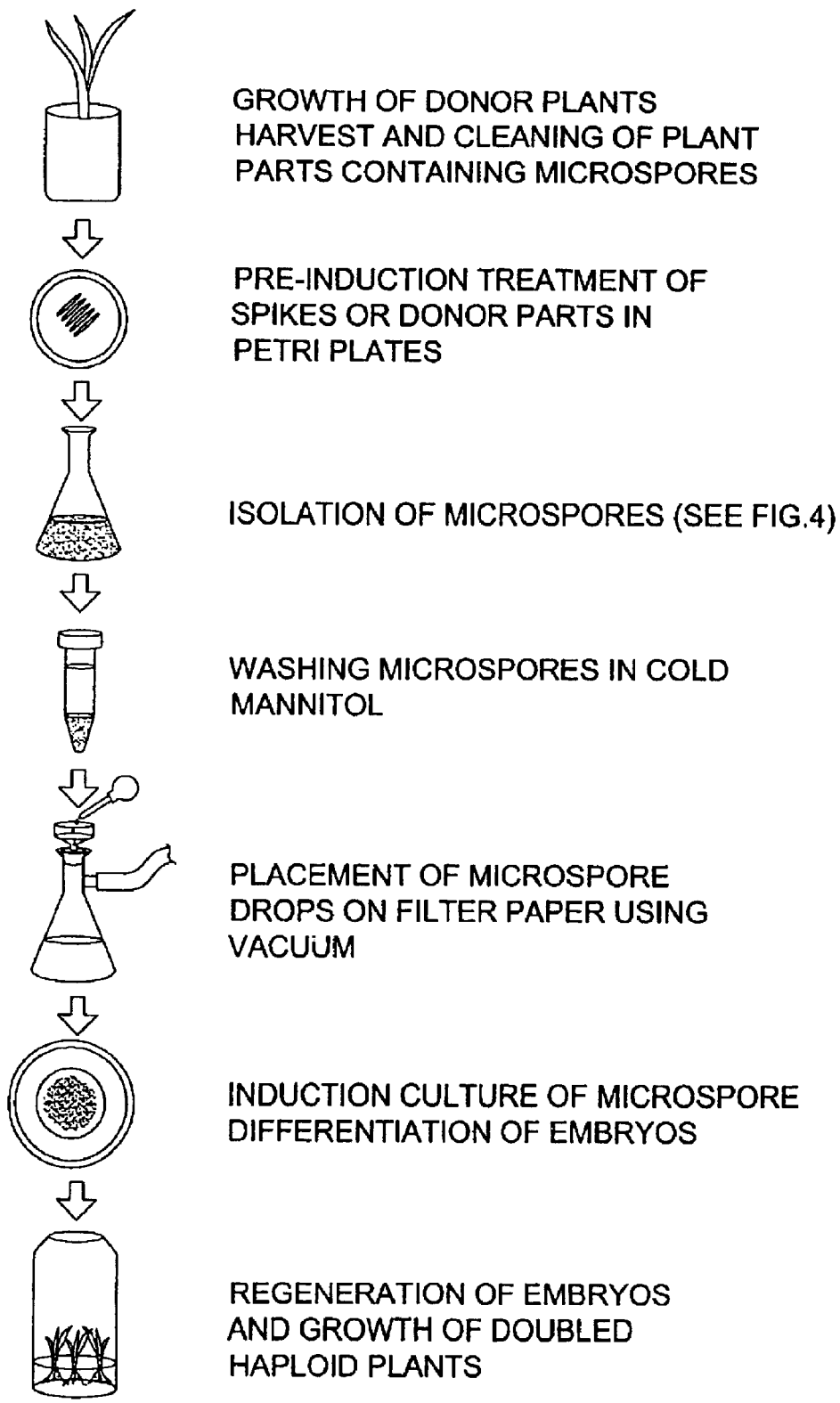
FIG. 1 is a flow diagram representing a method according to an embodiment of the invention.
Figure 2:
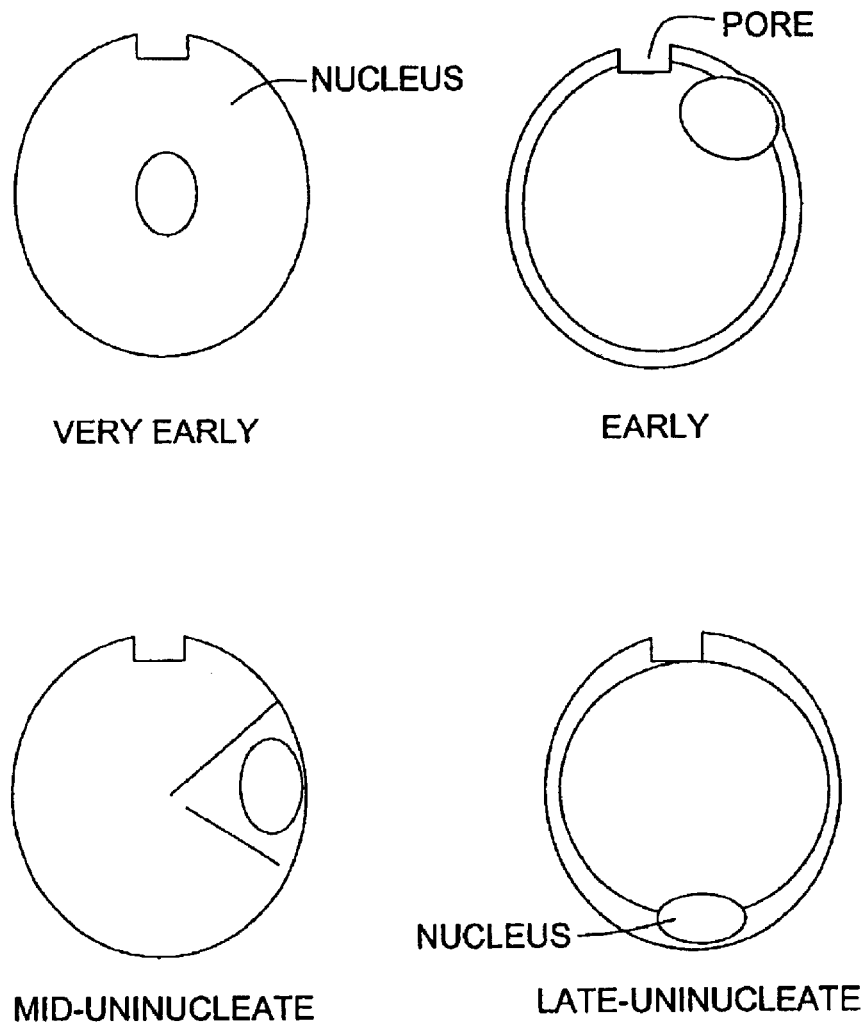
FIG. 2 is an illustration of uninucleate microspore development stages for timing of collection of plant segments. The lower figures arc DAPI stained microspores at the mid- or late uninucleate stages, when material is collected as described herein.
Figure 3:
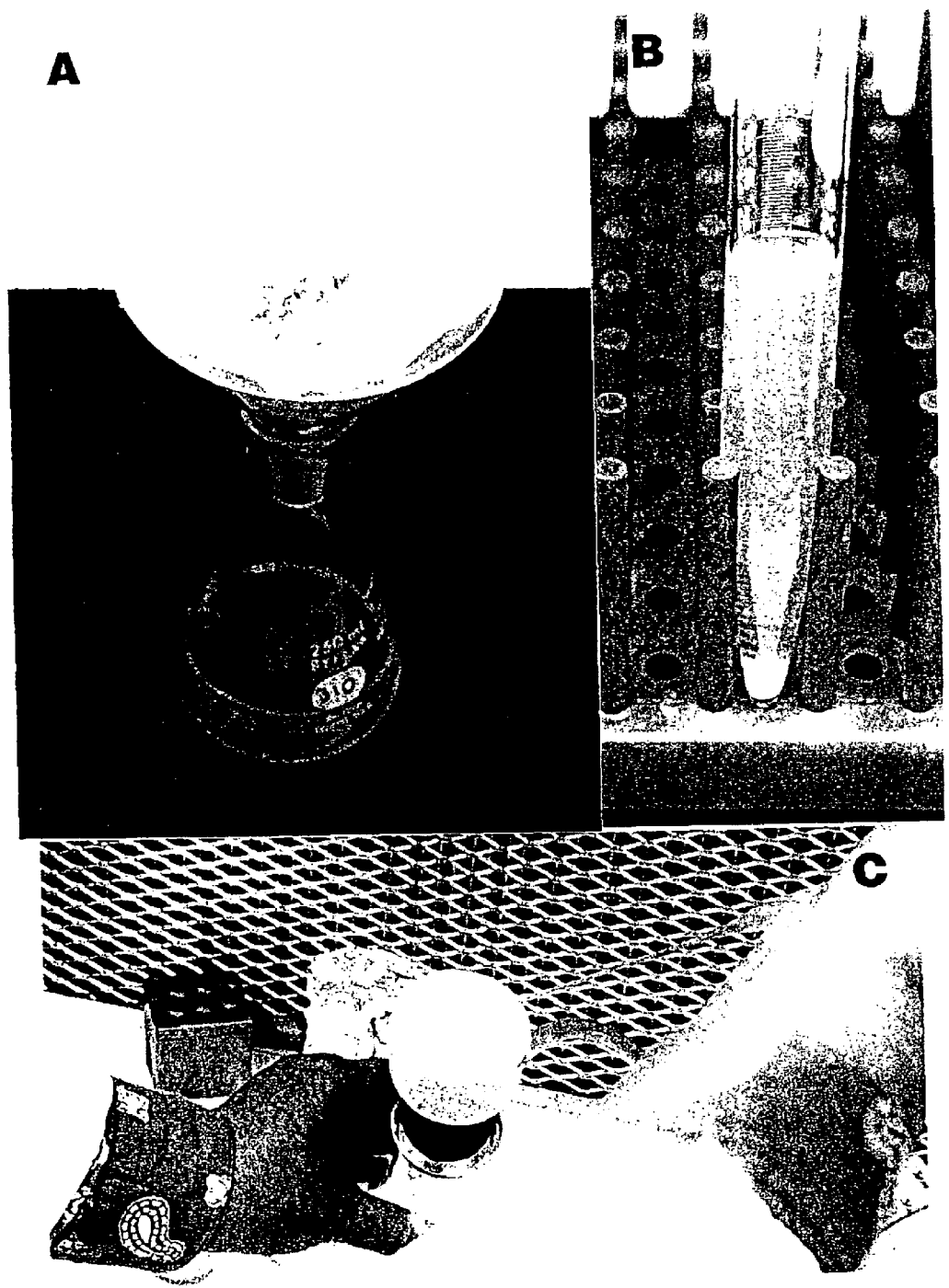
FIG. 3 shows the isolation and plating of microspores.

According to the invention, and as illustrated in the flow diagram of FIG. 1, there is provided a method of producing an embryo comprising the steps of (a) harvesting a microspore-containing plant segment from a donor plant; (b) incubating the segment under pre-treatment conditions to maintain a substantial portion of microspores at a uninucleate cell cycle G1 phase; (c) isolating microspores from the segment; and (d) incubating said isolated microspores in an induction medium comprising arabinogalactan protein and amino acids to induce embryogenesis, thereby producing embryos.

Further, the invention relates to a method of plant regeneration from microspores comprising the steps of (a) harvesting a microspore-containing plant segment from a donor plant; (b) incubating said segment under pre-treatment conditions to maintain a substantial portion of microspores at a uninucleate cell cycle G1 phase; (c) isolating microspores from the segment; (d) incubating the isolated microspores in an induction medium comprising an auxin, high glutamine levels and amino acids to induce the production of embryos; (e) incubating the embryos in a differentiation medium to produce differentiated embryos; and (f) regenerating plants from the differentiated embryos.

Plant Growth

According to the present invention, it is desired that donor plants are grown in a controlled environment, which is preferably pest free, but the invention is not restricted to plants produced under these growth conditions. The following controlled environment growth conditions are exemplary, but are not to be considered limiting in any manner.

Optimal relative humidity may range from about 50% to about 90%, preferably from about 60% to about 80%. Light is provided at about 300 $\mu E$ $m^2s$ to about 450 $\mu E$ $m^2s$, preferably at about 350 $\mu E$ $m^2s$ to about 400 $\mu E$ $m^2s$ at pot level. Any acceptable source of light may be used, for example, cool-white Gro-Lux™ bulbs, incandescent bulbs, or a combination thereof. The plants may be grown hydroponically.

More consistent yields of embryos and green plants arise from microspores produced in plants that have not been subject to water drought, stress or pest infestation, or any combinations thereof. Stressed plants produced through under or overwatering, or pest infestation, often produce microspores that respond inconsistently or that may fail in culture.

The following temperatures result in optimum plant growth. For winter barley, about 13 to about 17° C., preferably about 15° C., in the light for a duration of about 15 to about 18 hours, preferably from about 16 to about 17 hours, per day. During the dark cycle, having a duration of about 6 to about 9 hours, and preferably from about 7 to about 8 hours per day, optimum temperatures range from about 10 to about 14° C., preferably about 12° C.

For spring barley grown under a light cycle having a duration of 15–18 hours, preferably 16–17 hours, temperatures may range from 16–20° C., preferably 18° C. During a dark cycle having a duration of 6–9 hours, and preferably 7–8 hours per day, optimum temperatures for spring barley range from 13–17° C., preferably 15° C.

For winter or spring hexaploid wheats, grown under a light cycle having a duration of 15–18 hours, preferably 16–17 hours, temperatures may range from 16–25° C. During a dark cycle having a duration of 6–9 hours, and preferably 7–8 hours per day, optimum temperature for hexaploid wheat range from 13–18° C., preferably 15–16° C.

Plants may be fertilized weekly to optimize growth. Spraying with pesticide near the time of collection is avoided, since such spraying may eliminate microspore response. However, plants may be sprayed at earlier stages to minimize any insect or fungal infestation.

Microspore Staging

Microspore-containing plant segments, such as for example tillers, spikes, panicles, anthers, florets or tassels are collected from donor plants when the oldest microspores are at the mid to late uninucleate stage.

Optionally, a sample of microspores from the microspore-containing plant segment may be examined to ensure the appropriate stage of development. Descriptions of mid to late uninucleate stage can be found in publications such as Wheatly et al. (Plant Cell Rep 1986;5:47–49), which document is incorporated herein by reference. One of the clearest staging features is the location of the nucleus relative to the microspore pore (see FIG. 2). In the early uninucleate stage, the nucleus is near the pore and by late uninucleate, it is opposite the pore. The staining of barley microspores with aceto-carmine or DAPI may be used to illustrate this feature. Alexander's stain may be used to illustrate this feature in microspores derived from wheat and maize.

In the case wherein the microspore-containing plant segment is a tiller, spikes are removed from the tiller sheath. Microspores derived from a floret located at the central part of a spike may be examined by staging to determine stage of development. Microspore-containing plant segments may then be selected having microspores which are close to the mid to late uninucleate stage based upon their developmental similarity to those assessed by staining. Optionally, upon removal from the sheath, the spikes may be selected further based on a consistent length and floret appearance as compared to the segment examined.

Initial Treatment of Microspore-containing Plant Segment

Selected microspore-containing plant segments having microspores which are in the mid to late uninucleate stage are then placed in Perri plates (eg. 15×100 mm) for initial treatments, prior to the pre-treatment which is described below in further detail.

Optionally, microspore-containing plant segments may be cleaned with a cleaning solution. Appropriate cleaning solutions include ethyl alcohol solutions having from about 50% to about 80% ethanol, preferably about 70% ethanol, or aqueous solutions comprising about 10% to about 15% bleach (about 0.5% to about 1.0% chlorine).

For example, which is not to be considered limiting in any manner, cut tillers may be sprayed with an aqueous solution of about 70% ethanol prior to removal of the spikes. In barley, the awns may then be pulled off and the spices undergo a pre-treatment, as described in detail below. In wheat, if awned, the awns may be cut off but not too close as exposing the inside of the floret to cleaning solutions may be deleterious.

As a further example, which is not to be considered limiting in any manner, if awns or spikes have emerged from the leaf sheath or if contamination is a problem, spikes may be sterilized by placing them in a glass jar and covering them for 10–23 minutes with a solution of about 10% bleach. Isolated anthers are not treated with bleach. After cleaning, the florets or spikes are rinsed well with water and residual moisture is allowed to evaporate before incubation in the mannitol solution. Cleaning may be conducted in a Flow Bench to ensure adequately clean conditions.

As a further option during initial treatment, selected microspore-containing plant segments may undergo post-harvest incubation in ice water at a temperature of from about 3° C. to about 6° C., preferably at about 4° C. for a duration of up to 4 weeks, for example from 3 to 4 days to 3 to 4 weeks. For example, spikes may be incubated in sterile water in a petri dish (about 0.5 ml water per plate) at a temperature of about 4° C., for about 2–4 weeks. This incubation may be conducted, if for example, a segment is harvested before microspores are at an appropriate stage of development. Thus, the post-harvest incubation may continue until an appropriate microspore stage is reached for the segment to proceed to pre-treatment, which may be determined by staining. For example, tillers may be incubated in ice water until spikes are removed from the sheath. The post-harvest incubation period should be minimized to avoid microspore stage progression during this period.

Pre-treatment

Pre-treatment of microspore-containing plant segment is conducted to align microspores at a similar stage of development in preparation for embryogenic induction. Pre-treatment incorporates cold conditions in combination with incubation of plant segments in sterile water or in a sterile aqueous solution of sugar alcohol. In some species this pre-treatment may require the addition of media macro-salts.

Pre-treatment may last for between about 3 days to about 4 weeks, depending on the conditions implemented. If water is used during the cold incubation, the duration of pre-treatment may range from about 1 week to about 4 weeks depending upon species and genotypes. If a sugar alcohol solution is used, a shorter incubation period of from about 3 to about 5 days may be employed, with 3 days preferred for transformation procedures.

For pre-treatments in a sugar alcohol solution, the concentration of sugar alcohol may range from 0.1 mol/liter to about 1.0 mol/liter. Preferably, the sugar alcohol is present in a quantity of from about 0.2 mol/liter to about 0.5 mol/liter, and more preferably at a level of about 0.3 mol/liter, for barley or 0.4 mol/liter for wheat. The sugar alcohol may be selected from any in the group comprising mannitol, maltitol, sorbitol, xylitol, of any combination thereof, and is preferably mannitol. Treatment of spikes with the preferable combination of cold (4° C.) plus mannitol incubation at 0.3 mol/liter for 3 days increases the yield of green regenerant plants from microspores.

The sugar alcohol is combined with the plant segments in a quantity adequate to partially cover segments arranged in a single layer, for example about 15 mL in a 15×100 mm Petri plate. For ice water treatment of spikes, only 0.5 ml of water is added to a 15×100 mm plate.

Petri plates are then sealed, for example with a film such as Parafilm™, and placed in the dark at a temperature of from about 3° C. to about 6° C., preferably at about 4° C. The incubation continues for a duration of from about 3 to 5 days, when incubated in a sugar alcohol solution, and for a duration of from about 10 days to about 4 weeks when incubated in ice water, depending upon the species.

Optionally, plant segments may be incubated at room temperature following the method by Roberts-Oehlschlger and Dunwell (1990)(about 22° C. to about 27° C., preferably at about 25° C.) in an aqueous solution having from about 0.2 mol/liter to about 0.5 mol/liter sugar alcohol, preferably having about 0.3 mol/liter sugar alcohol. This incubation for up to about 4 days, preferably for 3–4 days and is an effective induction trigger but does not maintain microspores at the uninucleate stage.

Microspore Isolation

Following pre-treatment, microspores are isolated from plant segments. If the plant segments are anthers, they can be vortexed for up to about 10 minutes, preferably for about 5 minutes, after which time most of the microspores will be shed, as disclosed previously by Kasha et al. (IAEA-SM-1995:340/9:23–37).

Sterilized (autoclaved) glassware and tools should be used within a Flow Bench, to pick up the plant segments after pre-treatment. Segments of spikes or tassels with florets are cut to reduce segment size to about 2 cm to about 3 cm in length. Cut segments are then combined with an ice-cold aqueous sugar alcohol solution having from about 0.2 mol/liter to about 0.5 mol/liter sugar alcohol, preferably about 0.3 mol/liter mannitol, to form a suspension. The suspension is blended at a speed adequate to release microspores from the residual plant segment.

If the suspension is to be blended, preferably, a chilled blender container is used. An adequate quantity of chilled sugar alcohol solution is added to the plant segments to cover the spike segment. By way of example, eight to ten 2-rowed barley spikes or four 6-rowed barley or wheat spikes may be combined with about 200–300 ml of sugar chilled alcohol solution in a blender container to provide sufficient microspores (500,000) for one culture plate. During blending, the plant segments and sugar alcohol solution are combined at low speed for up to about 15 seconds, preferably about 5–10 seconds. However, the appropriate blending time and speed, will vary depending on the genotype and pre-treatment, and will ultimately effect viability.

As an alternative to blending, a vortex isolation procedure may be used on isolated anthers when the number of spikes available is limited. This improves viability of microspores so obtained, since vortexing is less harsh than blending (see for example Kasha et al. IAEA-SM-1995:340/9:23–37).

The resulting microspore-containing slurry is quickly filtered and washed (see FIG. 3) in a solution of sugar alcohol, for example having about 0.2 mol/liter to about 0.5 mol/liter, preferably 0.3 mol/liter of mannitol. Caution to avoid plasmolysis of microspores should be employed, since embryos will not develop from plasmolyzed microspores. If microspore viability is below about 50%, dead microspores may be removed by placing the resuspended pellet on a density gradient, for example, a 20% maltose density gradient followed by centrifugation, and the viable microspore fraction is retained.

Embryogenic Induction of Isolated Microspores

Following pre-treatment and isolation of microspores, microspores are then induced to develop into embryos. After the final wash of the microspore isolation step, the supernatant is decanted and the microspore pellet resuspended in an induction media. The induction media optimizes the response of the plant to induce embryogenesis.

The induction medium may comprise any plant culture medium having adequate macro and micro salts to support viable microspores, to which an auxin has been added. Exemplary media, which are not to be considered as limiting in any manner for use as induction media are outlined in Table 1. These media are based on FHG medium, as disclosed by Hunter (1987), and MS medium, as disclosed by Murashige and Skoog (1962). These basic media have been modified for use with barley (MFHG) and wheat (MMS4) respectively.

One possible auxin which may be added to either basic medium according to the invention is PAA (phenylacetic acid), which is effective in providing an induction response (Ziauddin et al. 1990). In the exemplary composition outlined in Table 1, which is not to be considered limiting, the induction medium combines high levels of glutamine, maltose as the sugar and has PAA as the auxin.

TABLE 1

Culture Media Composition

| Media components | FHG Media mg/L | | MS Media mg/L | |
| --- | --- | --- | --- | --- |
| | Basic | MFHG | Basic | MMS4 |
| *Macro salis* | | | | |
| $KNO_3$ | 1900 | 1900 | 1900 | 1400 |
| $NH_4NO_3$ | 165 | 165 | 1650 | 300 |
| $KH_2PO_4$ | 170 | 170 | 170 | 170 |
| $MgSO_4.7H_2O$ | 370 | 370 | 370 | 370 |
| $CaCl_2.2H_2O$ | 440 | 440 | 440 | 440 |
| $FeSO_4 7H_2O$ | — | — | 27.8 | 27.8 |
| *Micro salis* | | | | |
| $FeNa_2.EDTA$ | 40 | 40 | 37.3 | 37.3 |
| $MnSO_4.5H_2O$ | 22.3 | 22.3 | 22.3 | 22.3 |
| $H_3BO_3$ | 6.2 | 6 2 | 6.3 | 6.3 |
| $ZnSO_4.7H_2O$ | 8.6 | 8 6 | 8.6 | 8.6 |
| $COCl_2.6H_2O$ | 0.025 | 0.025 | 0.025 | 0.025 |
| $CuSO_4.5H_2O$ | 0.025 | 0.025 | 0.025 | 0.025 |
| $NaMoO_4 2H_2O$ | 0.25 | 0.25 | 0.25 | 0.25 |
| KI | — | — | 0.83 | 0.83 |
| Other Components | | | | |
| Glutamine | 730 | 750 | 146 | 975 |
| Inositol | 100 | 100 | 1000 | 300 |
| Thiamine | 0.4 | 0.4 | 0.4 | 0.4 |
| Nicotinic Acid | — | — | 0.5 | 0.5 |
| Pyroxidine | — | — | 0.5 | 0.5 |
| Sucrose | — | — | 30.0 gm | — |
| Malrose | 62 gm | 62 gm | — | 90 gm |
| Phenylacetic acid | — | 10 | — | 4 |
| Indole acetic acid | — | — | 1.0 | — |
| BAP | 1.0 | 1.0 | — | — |
| Kinetin | — | — | 1.0 | 0.5 |
| AGP | — | 10 | — | 10 |
| Agarose | — | — | 8.0 gm | — |
| Phytagel | — | 3.0 gm | — | 3.0 gm |

The modified FHG medium (MFHG) may be used for the induction of barley isolated microspores while MMS4 may be used for wheat. Once the embryos show signs of green, both barley and wheat are typically regenerated in the original MS medium except that the kinetin is reduced, for example, but not limited to, about 0.5 mg/L kinetin. For the intermediate step of differentiation of embryos before regeneration in either barley or wheat, the appropriate induction media may be modified by reducing the maltose, for example, but not limited to about 30 gm/L, removing the auxin, changing the inositol, for example but not limited to about 250 mg/L, adding casein, for example but not limited to, about 1.0 gm/L, and adding proline, for example, but not limited to about 690 mg/L.

The induction media comprises an isotonic combination of salts, an amide, for example but not limited to, glutamine at a level of from 500 to about 1000 mg/liter, a sugar source, such as maltose, sucrose, or melobiose, or other sugars (see Hunter, 1988), at a level of from about 20 g/liter to about 100 g/liter. Auxin may be used at a level of from about 2 mg/liter to about 20 mg/liter, preferably from about 2 mg/liter to about 10 mg/liter. Auxin may be selected from, but not limited to PAA (phenylacetic acid), NAA, picloram, or 2,4-D. 2,4-D is a stronger auxin and would allow use of smaller amounts. An exemplary amount of PAA is from about 4 mg/liter to about 5 mg/liter of induction medium. However, if 2,4-D is used, it is optimally removed within about 1 to about 4 hours and replaced with PAA in order to get a high frequency of embryo formation.

Microspores are initially incubated in induction medium at a density which ensures adequate microspore division. By way of example, which is in no way to be considered limiting, a pellet containing about 500,000 barley microspores may be incubated on sterile and washed filter paper. Another example is 100,000 wheat microspores with ovary co culture on sterile and washed filter paper.

To improve the response of micro spores in the induction medium arabinogalactan protein, herein referred to as AGP may be added to the induction medium to improve the response of microspores, for example, those microspores isolated from cereals such as wheat or barley. The presence of AGP in the induction medium improves the viability of microspores in culture, both in the presence and in the absence of ovaries in co-culture. AGP may be added to the induction medium at levels ranging from about 1 mg/liter to about 100 mg/liter of induction medium, and preferably in the range of about 10 mg/liter to about 25 mg/liter. In the presence of AGP, an incubation period for induction of about 10 to about 14 days is optimal.

The pH of the induction medium is adjusted to a range of from about 5.6 to about 6.0, preferably about 5.8. The induction medium may optionally be solidified by addition of about 3 g/liter of a solidifying agent such as Phytagel™ or Gelrite™ to the basic liquid medium. When Gelrite™ is used, a higher levels of antibiotic or herbicide is required to achieve effective selection, as compared to Phytagel™.

For example, which in no way is to be construed as limiting, a sterilized #2 Whatman filter paper disc is placed on the vacuum platform of a vacuum filter flask. Preferably, the support is rinsed with a liquid auxin-free medium such as FHG medium, an aqueous solution of sugar alcohol (about 0.2 mol/liter to about 0.5 mol/liter, preferably about 0.3 mol/liter), or sterile distilled water (about 10 to about 20 mL). Under low vacuum, about 1 mL to about 2 mL of microspores in an auxin-free medium are pipetted dropwise onto the support.

In total, from about 500,000 to about 600,000 barley microspore embryos may be added to each support. For wheat microspores, a lower density of from about 50,000 to about 200,000 microspores per support is optimal. One of skill in the art could easily determine the optimal density of microspores for a given cereal variety on each support. The support must be of adequate pore size to allow passage of liquid therethrough while maintaining microspore embryos thereon.

At this stage, it is of further advantage to include ovary co-culture in the induction media for wheat. If ovaries are located among the microspores in induction media, embryo development improves. Ovaries may be isolated from spikes at the time when microspores are at the Uninucleate stage, and are stored in the cold on moist filter paper until used in co-culture with the isolated microspores. From about 4 to about 20 ovaries may be used per plate. In the presence of AGP, from about 4 to about 6 are sufficient to give good response of microspores. The ovaries are placed among the microspores.

The support having microspores, and optionally ovaries for wheat thereon, is transferred to plates containing a solidified regeneration medium, such as the modified FHG (WFHG) media (for barley) or MS (MMS4) media media (for wheat) outlined in Table 1 having regeneration medium components added thereto. The plates are sealed using a gas-exchangeable seal, for example using Parafilm™. More than two wraps of Parafilm may cause culture response failure, possibly due to lack of gas exchange. Alternatively, a covered small plate may be placed within a larger plate along with a small open plate containing drops of distilled water. In this embodiment, only the large outer plate is sealed.

For induction of embryos the sealed plates are place in the dark at a temperature of from about 22° to about 30° C., preferably about 26° C. for barley, and about 28° C. for wheat, for about 2 weeks to about 5 weeks. Drops of liquid induction medium may be added to the plates if the filter paper support dries out.

The microspores are plated onto a solidified induction medium, and embryos are grow to a size of from about 1 to about 2 mm size, which may take up to about four weeks. Smaller embryo structures may be left on the induction medium plate and a drop or two of freshly prepared induction medium are added to the plate. These structures may then be moved once adequate size is attained. Barley microspores may alternatively be cultured on either liquid or agarose solidified FHG (MFGH) or for wheat, MS (MMS4) liquid or solidified media.

Differentiation

Once embryos reach a size of from, about 1 mm to about 2 mm, they are transferred from induction medium to a differentiation medium for a week or two until shoots and roots are developed. Differentiation medium comprises isotonic salts, and may comprise sucrose at a level of up to 50 g/liter. One possible differentiation medium is outlined in Table 1, and comprises MMS4 medium having about 30 g of maltose, about 250 mg of inositol, about 1000 mg of casein, and about 690 mg of proline, in addition to the original MS media comprising thiamine, pyridoxine, nicotinic acid and BAP. No auxin is present in the differentiation medium. The differentiation medium is adjusted to a pH of from about 5.6 to about 6.0, preferably about 5.8. The medium is then solidified by addition of a solidifying agent such as Phytagel™ or Gelrite™ at a level of 3 g/liter.

A solidified FHG medium without auxin could also be used as a differentiation medium. The original MS medium is optimally used as the differentiation medium when using selection for Basta herbicide resistance in culture due to the low glutamine level, which is preferred for differentiation since high glutamine levels reduces the effectiveness of selection.

Regeneration

Differentiated embryos are transferred from the differentiation medium to a regeneration medium for regeneration of green double haploid plants.

Differentiated embryos are placed on Gelrite solidified differentiation medium, such as an MS medium, modified as shown in Table 1.

Once shoots appear, embryos are optionally transferred to a regeneration media based on MS medium, as outlined in Table 1. The embryos are continued in the dark for about 3 days to about 4 days and then under low light intensity for about 8 hours/day at a temperature of from about 20° C. to about 25° C., preferably 22° C. Small plantlets (about 3 cm to about 4 cm tall) are transferred onto MS regeneration media without hormones in large vials or vessels to allow plants to grow. Once a plant has about 3 to 4 leaves, it is placed under strong light for conditioning for about 2 days to about 5 days. After about 2 days to about 5 days, small plants are transferred to soil or porting media in pots.

Transformation

Transformation of a plant with a gene of interest may be accomplished using the method as described herein, by incorporating the step of introducing a transgene into microspores after the pre-treatment. Because the pre-treatment brings microspores to a stage in the cell cycle prior to nuclear division, the addition of a transgene at this stage would allow for later duplication and division of the transgene, thereby leading to doubled haploid plants which are homozygous for the transgene. To test for transformation, any suitable detectable marker may be associated with the transgene, for example a herbicide resistance gene such as Bar (Jähne et al. 1994; Yao et al. 1997) or an antibiotic resistance gene may be used. Alternatively, a visible marker such as green fluorescent protein (GFP) may be used (Carlson 1998).

Transformation of microspores may be carried out using established methods involving either particle bombardment (e.g. Jahne et al. 1994; Yao et al. 1997; Carlson 1998; Yao and Kasha 1998; all of which are incorporated herein by reference) or Agrobacterium mediated transformation (e.g. WO 96/29419; or EP 0 737 738 which are incorporated herein by reference). Preferably pretreated, freshly isolated microspores are used for transformation. Using the methods as described herein increased transformation frequencies have been observed. By using the process of combined cold and sugar alcohol pretreatment as described herein, microspores are maintained at the uninucleate G1 phase thereby permitting the production of homozygous transgenics.

By "gene of interest" it is meant any gene that is to be expressed within a host organism. Such a gene of interest may include, but is not limited to, a gene whose product has an effect on plant growth or yield, for example a plant growth regulator such as an auxin or cytokinin and their analogous, or a gene of interest may comprise a herbicide or a pesticide resistance gene, which are well known within the art. A gene of interest may also include a gene that encodes a pharmaceutically active protein, for example growth factors, growth regulators, antibodies, antigens, their derivatives useful for immunization or vaccination and the like. Such proteins include, but are not limited to, interleukins, insulin, G-CSF, GM-CSF, hPG-CSF, M-CSF or combinations thereof, interferons, for example, interferon-α, interferon-β, interferon-τ, blood clotting factors, for example, Factor VIII, Factor IX, or tPA or combinations thereof. A gene of interest may also encode an industrial enzyme, protein supplement, nutraceutical, or a value-added product for feed, food, or both feed and food use. Examples of such proteins include, but are not limited to, proteases, oxidases, phytases, chitinases, invertases, lipases, cellulases, xylanases, enzymes involved in oil biosynthesis etc.

Methods of regenerating whole plants from embryos are also known in the art. In general, transformed microspores are cultured in an appropriate medium as described herein, which may contain selective agents such as antibiotics, where selectable markers are used to facilitate identification of transformed microspores, to produce transgenic embryos. Transgenic embryos are readily grown into transgenic plants.

The above description is not intended to limit the claimed invention in any manner, furthermore, the discussed combination of features might not be absolutely necessary for the inventive solution.

Examples are provided below which describe particular embodiments of the invention. The examples are not to be construed as limiting, but rather the invention encompasses such modifications to the exemplified embodiments as would occur to one skilled in the art.

EXAMPLE 1

The following procedure is used to isolate microspores from a slurry obtained by blending or vortexing plant segments. The slurry is filtered through cheese cloth or a coarse nylon membrane (FIG. 3A). The filtrate is collected and may be re-filtered through a nylon mesh, of for example 100 μm mesh, into a centrifuge tube. The centrifuge tube is then centrifuged under conditions adequate to pellet the microspores (FIG. 3B), for example which is not to be considered limiting in any manner, at about 900 rpm for 5 minutes. About 0.15 ml of pellet may yield approximately 500,000 barley microspores. The microspore pellet is resuspended in a cold aqueous solution of mannitol (about 0.2 mol/liter to about 0.5 mol/liter, preferably 0.3 mol/liter mannitol) and is washed until the wash supernatant does not show a green tinge. For examples, 2–3 washes may be employed for this purpose. The pellet is then suspended in induction medium and drop by drop filtered onto the filter paper using vacuum filtration (FIG. 3C).

EXAMPLE 2

Figure 4:
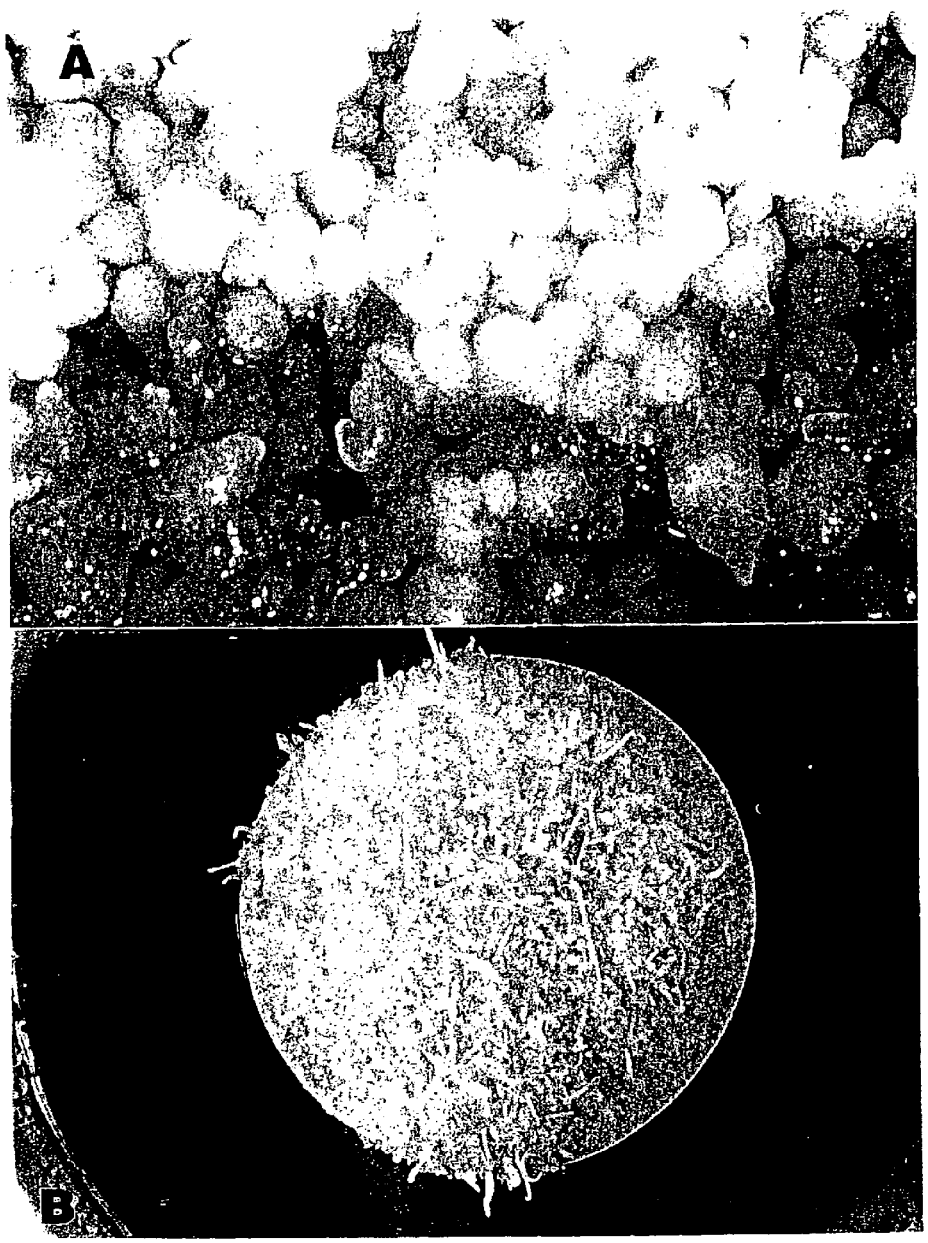
FIG. 4 illustrates embryo development of barley c.v. Igri. microspores on filter paper in the absence of AGP.
Figure 5:
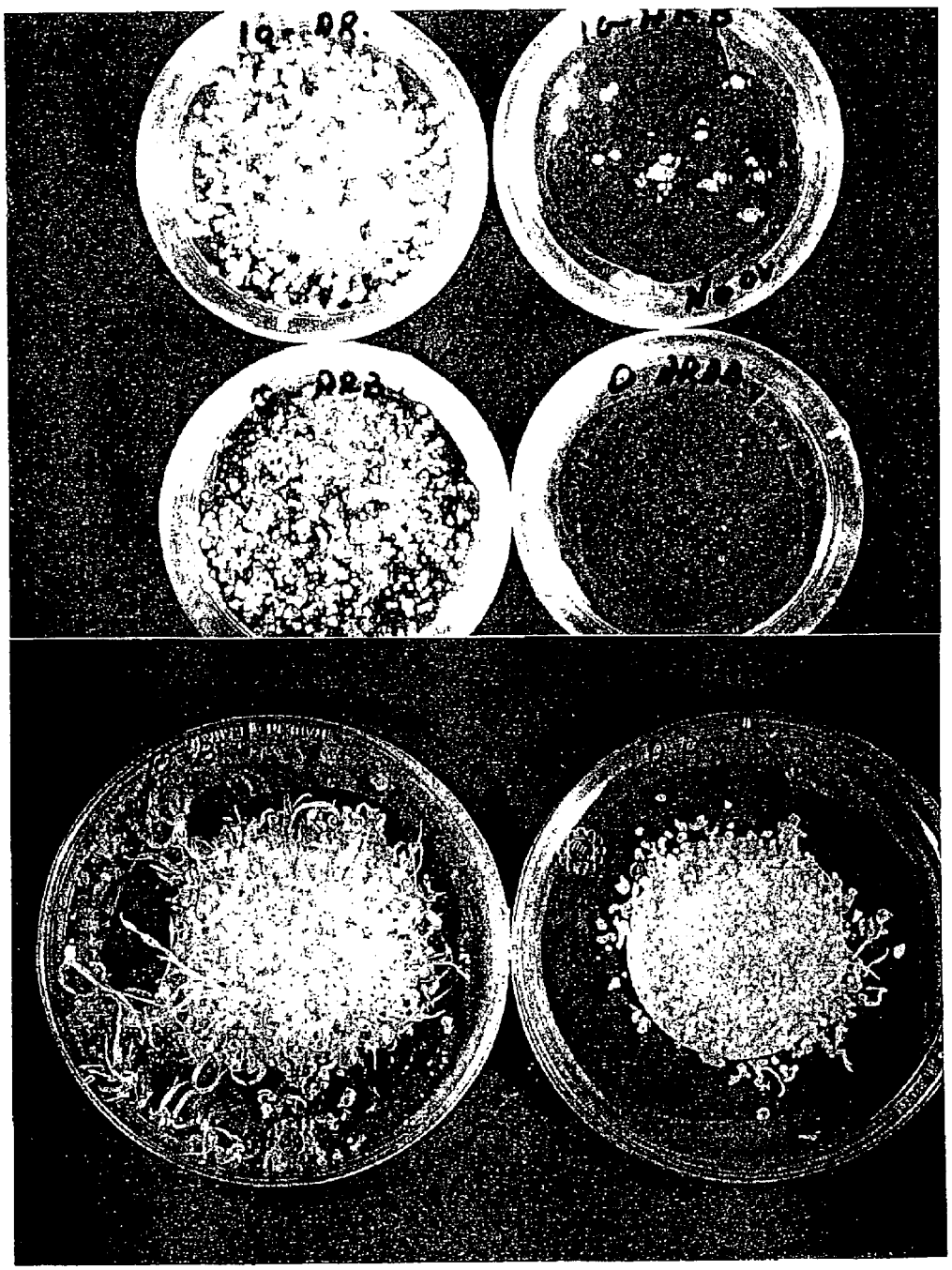
FIG. 5 shows embryo development in wheat and barley.

Embryogenesis from thirty different barley genotypes was conducted according to the procedure in accordance with the present invention. Between 10,000 to 15,000 embryos were usually produced per plate. Table 2 illustrates some counts of embryos based on an average of three replications (plates). Not all thirty genotypes were counted. However, response of each genotype was judged on the basis of the appearance of plates after two weeks and again after 4 to 5 weeks. Random samples of 500 embryos were taken from the counted plates and placed on regeneration media to estimate the embryo regeneration ability. As seen in Table 2, the number of regenerants ranged from 36 to 97%. FIG. 4 illustrates barley c.v. Igri embryo development at 3 weeks (FIG. 4(a)) and 5 weeks (FIG. 4(b)) on filter paper placed on solidified induction media.

TABLE 2

Embryo induction and regeneration following pretreatment of various genotypes in barley

| Genotype | Pretreatment | Embryoids* | % embryoid Regeneration |
| --- | --- | --- | --- |
| Igri | 28 d cold, 4° C. | 13136 | 85% |
| | 4 d 0.3M. man. 4° C. | 12380 | 97% |
| | 4 d 0.3M. man. 25° C. | 13504 | 88% |
| GBC 782 | 3 d 0.3M man. 4° C. | 14496 | n.a. |
| GBC 783 | 3 d 0.3M man. 4° C. | 11360 | n.a. |
| Harrington | 3 d 0.3M man. 4° C. | 5533 | 36% |
| Lina | 21 d cold 4° C. | 15377 | 77% |
| | 7 d 0.3M man 4° C. | 8921 | 81% |
| Oxbow | 21 d 0.3M man. 4° C. | 10810 | 58% |
| Manley | 4 d 0.3M man. 4° C. | 11360 | 74% |
| GBC 777 | 4 d 0.3M man. 4° C. | 14133 | 89% |
| GBC 778 | 4 d 3.3M man. 4° C. | 7667 | 84% |

*Embryo numbers are the average from 3 plates while % regeneration is based on shoots formed on 500 embryos per plate.

Barley genotypes Igri. GBC777 and GBC778 are winter growth habit while the remainder in Table 2 are spring habit genotypes. Harrington, Manley and Oxbow are the predominantly grown 2-row malting barleys in Canada at present. Igri and Lira are of European origin. Lines GBC 777 and 778 are 6-row barley.

Three different pre-treatments were compared within the genotype Igri and no apparent differences were observed relative to embryo induction or regeneration (Table 2). Lina normally responds well in microspore culture following a mannitol pre-treatment, but in this study using the combination of cold plus mannitol for 7 days, response was low. Thus, embryo formation was also counted in Lina when a 21 day cold pretreatment had been used and this response was more typical of Lina (Table 2). The regeneration response from the two pretreatment methods on Lina was similar. The frequency of fertile doubled haploids among the Lina progeny following the two pretreatments was not different, namely 79% after the combination 7-day treatment and 83% after the 21 day cold pretreatment.

The response from Harrington was also low in both embryo formation as well as in overall percentage regeneration, but has since been observed to be improved. The response of Oxbow showed that at the shorter times of pre-treatment, good response was observed, but the induced structures mostly became callus. However, when the longer pretreatment was used as shown in Table 2, the response was mostly embryogenic and resulted in an acceptable rate of overall regeneration. This response is typical of Oxbow, possibly due to a higher endogenous auxin level.

The 6-row winter habit genotype GBC777 was unusual in that it only produced about 5% green plants, the remainder being albino. Even at that low rate, it would still be possible to obtain about 500 green plants per plate if all embryos were regenerates. Although such a procedure would be laborious, it would be possible to transfer all embryos to a suspension culture in regeneration media and low light to recover the green germinating embryos.

Embryogenesis was visually assessed in barley winter genotypes; OAC Elmira, GBC776, GBC779, GBC780 and GBC781, and spring genotypes, Trinity, Cooper, Golden Promise, Disa, Morex, Excel, Elrose, Bruce, Rodeo, H936 and Sabarilis. Effective embryogenesis was achieved with the cold plus mannitol pre-treatment over 3 to 4 days in 0.3 mol/liter mannitol at 4° C. on these genotypes. Under these conditions about 2,000 plants per $10^5$ microspores, or about 200 plants per spike on responsive genotypes has been observed.

The method of embryogenesis for microspores according to the invention is effective for barley across a wide range of genotypes. In the above-noted barley genotypes, the production of embryo structures led to a high percentage of regeneration initiation.

EXAMPLE 3

The effect of the duration of pre-treatment on embryogenesis from barley genotype Igri for spikes incubated with 0.3 mol/L mannitol at 4° C. Table 3 illustrates that as few as 4 days of pre-treatment drastically effects the number of embryos formed from microspores. Although the number formed increases up to 28 days of pre-treatment, only a 4 day period is required to achieve beneficial effects. It was found that duration of pre-treatment was not critical to achieving effective response in Igri. However, duration of pre-treatment did appear to effect Oxbow as previously mentioned, and as illustrated in Table 2.

TABLE 3

Effect of duration of pretreatment on embryo formation from spikes at 4° C. in 0.3 mol/liter mannitol

| Days in Pretreatment | # Embryos formed |
| --- | --- |
| 0 | 0 |
| 4 d | 9579 |
| 7 d | 9693 |
| 14 d | 8981 |
| 21 d | 9692 |
| 28 d | 10213 |

EXAMPLE 4

The influence of the use of a support in culture media on the development of embryos and regeneration of plants from wheat microspores was examined in wheat microspores using genotype Chris. Microspores were incubated in induction medium (MMS4 medium), either on a support (Watman #2 filter disk) or in liquid medium (drop method). The preparation and use of filter paper has been described above. The drop method is prepared the same way, except the desired number of microspores are in a concentrated drop of liquid media which is put directly on top of the solid media After 10 days to 2 weeks, a drop or two of fresh liquid media is added to both the filter and drop system to help spread out the developing microspores so that more can develop. Table 4 illustrates the results obtained from three replications. Examples of development are shown in FIG. 4.

TABLE 4

The influence of culture media support system on the development of embryos and the regeneration of plants from wheat microspores (Genotypes Chris) induced on $MMS_4$ (without AGP).

| Treatment | Plate # | # ELS | gr. Plant | albino | Total | % regen. | % gr. reg. |
| --- | --- | --- | --- | --- | --- | --- | --- |
| Filter | 1 | 650 | 350 | 4 | 354 | 54 | 54 |
|  | 2 | 615 | 265 | 3 | 268 | 44 | 43 |
|  | 3 | 658 | 390 | 5 | 395 | 60 | 59 |
|  | total | 1923 | 1005 | 12 | 1017 | 53 | 52 |
| Drop | 1 | 300 | 130 | 2 | 132 | 44 | 43 |
|  | 2 | 300 | 100 |  | 100 | 33 | 33 |
|  | 3 | 300 | 110 | 3 | 113 | 38 | 37 |
|  | total | 900 | 340 | 5 | 345 | 38.3 | 37.7 |

More than twice as many embryos were induced per plate using a support during induction treatment than using incubation in liquid induction medium. The number of green plants obtained was more than doubled by the use of a support during induction, which translates into a higher percentage of regenerated plants from embryos. The better development on the filter may result from better aeration on the filter paper. The pretreatment, isolation of microspores and media are the same for both induction and regeneration.

These results demonstrate the benefit of using a support during embryogenic induction of microspores. Examples of development are shown in FIG. 4.

EXAMPLE 5

A comparison of regeneration media composition was conducted for wheat microspores induced on a medium in the presence and absence AGP. The regeneration medium was based on MMS4 medium having either 3% sucrose or 9% maltose as a sugar source, or in an AGP-containing medium based on MMS4 with 9% maltose. The microspores were either induced on a support, in this case, a Watman #2 filter disk, or were placed on a solid media in liquid drops.

TABLE 5

Influence of Regeneration Media on Plant Development from Wheat (cv. Pavon 76) Microspores induced on AGP media, either on filters (A) or as drops on solid media (B), 4 reps (Plates).

| Regen. Media | # ELS | # Green Plants | # Albino | % regen. | % regen green |
| --- | --- | --- | --- | --- | --- |
| A |  |  |  |  |  |
| $MMS_4(S^*)$ | 498 | 385 | 10 | 79.3 | 77.3 |
| $MMS_4(M^*)$ | 498 | 235 | 22 | 51.6 | 47.2 |
| AGP(M) | 498 | 148 | 17 | 33.1 | 29.7 |
| Totals | 1494 | 768 | 49 | 54.7 | 51.4 |
| May Transf.** | 600 | 291 | 17 | 51.3 | 48.5 |
| B |  |  |  |  |  |
| $MMS_4(S)$ | 260 | 172 | 6 | 68.5 | 66.2 |
| $MMS_4(M)$ | 260 | 122 | 9 | 50.4 | 46.9 |
| AGP(M) | 265 | 103 | 10 | 42.6 | 38.9 |
| Totals | 785 | 397 | 25 | 53.8 | 50.6 |
| May Transf.** | 610 | 296 | 9 | 50.3 | 48.5 |

*Sugar is 3% sucrose (S), vs. 9% maltose (M)
**Later May transfer was from the MMS4 media only, and at that time there were another 650 to 750 smaller ELS that were not transferred.

As can be seen in the results provided in Table 5, the presence of a filter support resulted in increased embryogenesis and green plant production, as compared to induction of embryos in a liquid media dropped onto a solidified medium. Sucrose within the regeneration media was effective in producing a high percentage of green plants, however maltose was also found to be effective. Without wishing to be bound by theory, this may be due to the quicker release of energy from sucrose that is required for regeneration. The addition of AGP to the regeneration media reduced the number of green plants produced. This result may indicate that AGP is important in the initial stage on induction media but not at later stages.

EXAMPLE 6

The effect of AGP on embryogenesis and plant regeneration was assessed in wheat microspores which were isolated from genotype Pavon 79 according to the method of the present invention. Embryogenesis results are presented in Table 6 and plant regeneration data is provided in Table 7. AGP levels of 0, 1, 5, and 10 mg/liter were tested.

Figure 6:
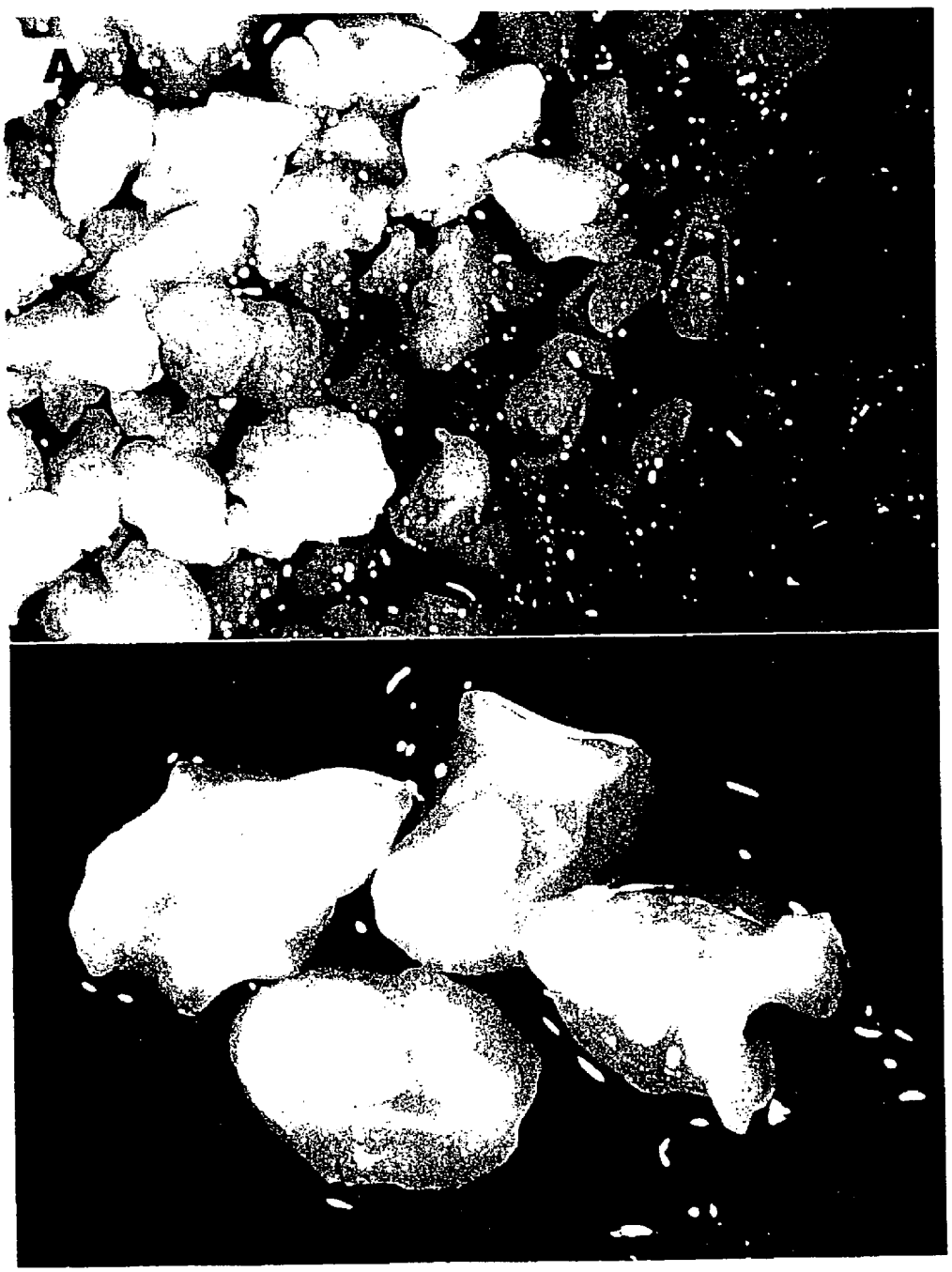
FIG. 6 illustrates good embryo development in wheat after 4 weeks in culture with AGP and ovary co-culture.

To obtain regeneration data as shown in Table 7, 250 embryos from one plate were transferred to regeneration media. A significant improvement in embryogenesis, regeneration and % green plant production resulted from the addition of 10 mg/L of AGP, using the genotype Pavon 79. Pavon 79 shows a higher frequency of albino plants than other genotypes. Additionally, the data illustrates the presence of ovaries in co-culture enhanced embryogenesis and plant regeneration. Only at 10 mg/liter of AGP was significant embryogenesis observed in the absence of ovary co-culture. FIG. 5(a) illustrates the comparative response of wheat microspores to the presence or absence of wheat ovaries and 0 or 10 mg/L AGP. FIG. 6 illustrates the good embryo structure developed in wheat after 4 weeks on medium with ovaries and AGP.

TABLE 6

Response of wheat isolated microspore cultures to varying levels of AGP in MMS4 medium, with and without ovaries. Two Reps of cv Pavon 79.

| Treatments | | Total # Micro | # alive and | # alive not | # dead micro | | #multi- cell | |
|---|---|---|---|---|---|---|---|---|
| AGP mg/L | ovary +/− | spores D 10 | dividing d 10 | dividing d 10 | spores d 10 | # multi- cellular d 10 | burst d 10 | # embryos 30 days |
| 0 | − | 102805 | 6930 | 5775 | 83500 | 6600 | 0 | 0 |
|  | + | 105925 | 16305 | 4950 | 68345 | 12850 | 1125 | 1650 |
| 1 | − | 89825 | 22125 | 5650 | 47558 | 13750 | 400 | 0 |
|  | + | 92575 | 22605 | 2805 | 47175 | 18500 | 1072 | 2130 |
| 5 | − | 98015 | 26152 | 8275 | 34500 | 28345 | 742 | 0 |
|  | + | 102280 | 18272 | 7600 | 30250 | 39078 | 7080 | 3393 |
| 10 | − | 110745 | 33275 | 6250 | 24650 | 41950 | 4620 | 50 |
|  | + | 108305 | 8500 | 0 | 23550 | 68000 | 15452 | 4250 |

Numbers at day 10 were estimated by counting them in a square area and multiplying by $1.65 \times 10^3$. Three areas were counted per plate and averaged, then the 2 reps were averaged. To estimate the numbers of embryos at day 30, one quarter of the plate was dissected and counted including all sizes of embryos.

TABLE 7

Regeneration plants from wheat microspores in the presence of AGP on induction media $MMS_4$, cv Pavon 79

| Treatments with ovaries and AGP mg/L | Total # of micro-spores | Total # of | Embryos transferred to Regn. | # of plants | | | % of green | % of |
|---|---|---|---|---|---|---|---|---|
| AGP | (×1000) | embryos | med. | green | Albino | Total | plants | regen. |
| 0 | 103 | 1650 | 250 | 37 | 78 | 115 | 32 | 46 |
| 1 | 90 | 2130 | 250 | 48 | 70 | 118 | 41 | 47 |
| 5 | 98 | 3393 | 250 | 50 | 70 | 120 | 42 | 48 |
| 10 | 111 | 4250 | 250 | 129 | 60 | 189 | 68 | 76 |

EXAMPLE 7

Preliminary experiments on both filter paper and on liquid media with ovaries were examined for embryo response in 0, 5 and 10 mg/liter of AGP in induction media. Table 8 shows the effect of AGP on Pavon 79 isolated microspore culture in liquid medium versus as grown on a filter paper support. The results are similar for liquid and filter paper at the 3 compared concentrations, and 10 mg/liter of AGP gave the best response.

TABLE 8

The effect of AGP on spring wheat Pavon 79 isolated microspore culture on MMS4 medium in liquid medium versus filter paper on solid media, both co-cultured with ovaries.

| AGP Conc. mg/L | # Microspores Cultured × 1000 | Total # Embryos/Plate |
| --- | --- | --- |
| 0 Liquid | 106 | 1650 |
| 0 Filter | ca 100 | 1769 |
| 1 Liquid | 93 | 2130 |
| 5 Liquid | 102 | 3393 |
| 5 Filter | ca 100 | 3080 |
| 10 Liquid | 108 | 4250 |
| 10 Filter | ca 100 | 4528 |

EXAMPLE 8

The effect of AGP on microspore embryogenesis in the presence of ovary co-culture was assessed using Chris and Pavon 79 wheat genotypes. Media comprising 5 mg/liter and 10 mg/liter of AGP were compared with a control medium, on microspore embryogenesis in the presence of ovary co-culture. The results in Table 9 indicate that overall response of Chris to AGP is higher than the response of Pavon 79.

TABLE 9

The effect of AGP on embryo development from microspores in spring wheat genotypes Chris and Pavon 79, using 0.8 ml drop on solid MMS4 medium with 3–4 ovaries.

| | Chris | | Pavon 79 | |
| --- | --- | --- | --- | --- |
| AGP Conc. mg/L | # of Reps | avg. # embryos | # of Reps | # embryos |
| 0 | 3 | 4007 | 3 | 2778 |
| 5 | 5 | 5618 | 3 | 4155 |
| 10 | 5 | 9836 | 3 | 4681 |

EXAMPLE 9

On the basis of data obtained in Example 8, Tables 8 and 9, illustrating that the highest concentration of AGP tested (10 mg/liter) resulted in the best response in embryogenesis, higher concentrations of AGP were then tested. In an experiment with Pavon 79, concentrations of 0, 10, 25, 50, 100, 500 and 1000 mg/L were used in microspore culture with 4 ovaries around a drop of liquid medium with microspores on top of solidified medium. The results are shown in Table 10.

TABLE 10

The effect of AGP concentrations on microspore culture of spring wheat Pavon 79 in MMS4 liquid media (4 rep average data)

| AGP Conc. mg/L | # at Day 12 | | | | | | Day 50 # of embryos |
| --- | --- | --- | --- | --- | --- | --- | --- |
| | Alive | Dead | Dividing | Multi cellular | ELS | Total Developing | |
| 0 | 64.3 | 62.7 | 12.4 | 23.5 | 2.1 | 38 | 2862 |
| 10 | 69.3 | 58.9 | 23.9 | 33.8 | 8.7 | 66.4 | 4493 |
| 25 | 66.6 | 69.3 | 13.6 | 38 | 10.3 | 61.9 | 3538 |
| 50 | 47.9 | 75 | 10.7 | 13.2 | 5 | 28.9 | 471 |
| 100 | 66.4 | 61 | 17.3 | 32.2 | 2.9 | 52.4 | 3709 |
| 500 | 57.3 | 61 | 19.4 | 27.7 | 4.5 | 51.6 | 3267 |
| 1000 | 69.3 | 56 | 14.8 | 28.5 | 7 | 50.3 | 1821 |

From the results obtained the AGP concentrations of 10 or 25 mg/liter illustrate optimal embryogenesis. However, higher concentrations can also be used. The microspore viability at day 12 was not significantly different from the control value with no AGP but the total number of developing structures improved in the presence of AGP. It was observed that 10 to 14 days in induction medium with AGP may be maximal as it appears that regeneration may be reduced with longer periods on medium with AGP.

EXAMPLE 10

The effect of AGP concentration during embryogenic induction of barley microspores in culture was examined. A wide range of concentrations was applied to microspores of cv. Igri as shown in Table 11. The AGP addition was effected by adding varying AGP concentrations in liquid FHG medium with $10^5$ microspores onto solid FGH medium. Using a drop of microspores on solidified MFHG medium, structures were counted under an inverted microscope. The proportion of alive and dead microspores was not estimated in these plates, but the developing microspores were much higher in the 0 mg control compared to wheat. Thus, the difference in response of barley to AGP at day 10 is not as pronounced as in wheat. However, similar to the results for wheat shown at day 50, the continued and more rapid development of the microspores with AGP was notable as seen in FIG. 5(b) at 4 weeks in culture.

TABLE 11

The effect of AGP on barley cv Igri isolated microspore development in liquid FHG medium after 10 days

| AGP Conc. mg/L | Dividing within microspore | Free Multicellulars | Total Developing |
| --- | --- | --- | --- |
| 0 | 33280 | 33310 | 65590 |
| 2 | 39600 | 33550 | 73150 |
| 5 | 43000 | 38230 | 81230 |
| 10 | 45280 | 35750 | 81030 |
| 25 | 39880 | 36030 | 75910 |
| 50 | 37120 | 39880 | 77000 |
| 100 | 42900 | 37730 | 80630 |
| 500 | 35890 | 37810 | 73700 |
| 1000 | 38500 | 41600 | 80100 |

EXAMPLE 11

The response of isolated microspores to embryogenesis and plant regeneration from spring and winter wheat genotypes was visually assessed using the method according to the present invention with AGP in the induction media. All genotypes responded to the method by producing embryos and green plants from microspores. Table 12 shows the relative response of each genotype, ranked on a scale of 0 to 3, wherein 0 represents no response, 1 represents a low response, 2 a good response, and 3 represents an excellent response. Both embryogenesis and green plant initiation were scored. In the winter genotypes, only 3 donor plants were available from a breeder so the sample was small.

TABLE 12

Evaluation of Isolated Microspore Culture across spring and winter wheat genotypes (response rated on a 0 to 3 scale)

| Genotypes tested | Response | |
|---|---|---|
| | Embryogenesis | Green plant regeneration |
| Spring wheats | | |
| Chris | 3 | 2–3 |
| Pavon 70 | 3 | 2–3 |
| Pavon 76 | 3 | 2–3 |
| Bob White S | 3 | 3 |
| Quantum | 3 | 1–2 |
| Hartog | 3 | 1–2 |
| Winter wheats | | |
| 2540 | 3 | 2 |
| OAC Montrose | 3 | 3 |
| Harus | 3 | 2 |
| Freedom | 3 | 2 |
| Hanover | 3 | 2 |
| Fundulea | 2 | na |
| AC Morley | 3 | 2–3 |

The induction response in wheat is genotype independent as it is in barley while the regeneration response is a little more variable. The results with the winter wheat lines are based on only 3 donor plants obtained from a breeder after vernalization. Regeneration of Fundulea was not conducted. Both Pavon and Bob White are quite variable cultivars and thus selections were cultured. Bob While S is an awnless selection. While induction in media without AGP is also good, the embryo development is not as good as with AGP and thus regeneration is strongly influenced by AGP.

All publications cited herein are incorporated by reference. Various modifications may be made without departing from the invention. It is understood that the invention has been disclosed herein in connection with certain examples and embodiments. However, such changes, modifications or equivalents as can be used by those skilled in the art are intended to be included. Accordingly, the disclosure is to be construed as exemplary, rather than limiting, and such changes within the principles of the invention as are obvious to one skilled in the an are intended to be included within the scope of the claims.

REFERENCES

Carlson, A. R. 1998. Visual selection of transgenic barley (*Hordeum vulgare L.*) structures and their regeneration into green plants. M.Sc. Thesis, Univ. of Guelph, 85pp.

Egertsdorter et al. Importance of arabinogalactan proteins for the development of somatic embryos of Norway Spruce *Picea abies. Physiol Plant* 1995;93:334–45.

Hunter, C. P. 1988. Plant regeneration from microspores of barley (*Hordeum vulgare L.*). PhD Thesis, Wye College, Univ. of London.

Jähne, A., D. Becker, R Brettschneider and H. Lörz. 1994. Regeneration of transgenic, microspore-derived, fertile barley. Theor. Appl. Genet. 89:525–533.

Kasha, K. J., Q. Yao, E. Simion, T. Ha, and R. Oro. 1995. Production and Application of Doubled Haploids in Crops. In: Induced Mutations and Molecular Techniques for Crop Improvement. IAEA/FAO Symp., Vienna. IAEA-SM-340/9:23–37.

Kawaguchi et al. A novel tetrasaccharide, with a structure similar to the terminal sequence of an arabinogalactan-protein, accumulates in rice anthers in a stage-specific manner. *Plant Journal*, 1996;9(6):777–785.

Kreuger et al. Arabinogalactan proteins are essential in somatic embryogenesis of *Daucus carota L. Planta* 1993;189:243–248.

Murashige, T. and F. Skoog, 1962. A revised medium for rapid growth and bioassays with tobacco tissue cultures. Physiol. Plant. 15:473–495.

Roberts-Oehlschlager, S. L. and J. M. Dunwell. 1990. Barley anther culture: Pretreatment on mannitol stimulates production of microspore-derived embryos. Plant Cell Tiss. Org. Cult. 20:235–240.

Wheatly W. G., A. A. Marsolais and K. J. Kasha. 1986. Microspore growth and staging for barley anther cultures. Plant Cell Rep. 5:47–49.

Yao, Q. A., E. Simion, M. William, J. Krochko and K. J. Kasha. 1997. Biolistic transformation of haploid isolated microspores of barley (*Hordeum vulgare L.*) Genome 40:570–581.

Ziauddin, A., A. Marsollais, E. Simion, and K. J. Kasha. 1990. Improved plant regeneration from wheat anther and barley microspore culture using phenylacetic acid (PAA). PLant Cell rep. 11:489–498.

The embodiments of the invention in which an exclusive property of privilege is claimed are defined as follows:

1. A method of producing an embryo comprising the steps of:
   (a) harvesting a microspore-containing plant segment from a donor plant;
   (b) incubating said segment under pre-treatment conditions in absence of colchicine, and at a temperature from about 3° C. to about 6° C., to maintain from about 50% to about 100% of microspores at a uninucleate stage of development;
   (c) isolating microspores from said segment; and
   (d) incubating said isolated microspores in an induction medium comprising arabinogalactan protein, to induce embryogenesis, thereby producing embryos.

2. The method according to claim 1, wherein said donor plant, in step (a) is a cereal plant.

3. The method according to claim 2, wherein said cereal plant is wheat or barley.

4. The method according to claim 1, wherein a said arabinogalactan protein in step (d) is present in said induction medium at a level of from about 1 mg/liter to about 100 mg/liter.

5. The method according to claim 4, wherein said arabinogalactan protein is present in said induction medium at a level of from about 10 mg/liter to about 25 mg/liter.

6. The method according to claim 5, wherein said arabinogalactan protein is present in said induction medium for about two weeks.

7. The method according to claim 1, wherein, in step (b), said microspores are at a uninucleate cell cycle G1 phase.

8. The method according to claim 1, wherein said pre-treatment conditions in step (b) comprise a temperature of from about 3° C. to about 6° C. for 3 to 10 days and incubation in an aqueous solution having from about 0.2 mol/liter to about 1.0 mol/liter of sugar alcohol.

9. The method according to claim 8, wherein said sugar-alcohol is selected from the group comprising mannitol, maltitol, sorbitol, xylitol, and any combination thereof.

10. The method according to claim 1, wherein said pre-treatment conditions in step (b) comprise incubation in water at a temperature of from about 3° C. to about 6° C. for 7 to 28 days.

11. The method according to claim 1, wherein, in step (a), said microspore-containing plant segment is selected from the group consisting of tillers, florets, spikes, anthers, pannicles and tassels.

12. The method according to claim 1, wherein said microspores, in step (d) are incubated in said induction medium for a period of from about 3 to about 14 days.

13. The method according to claim 1, wherein said induction medium, in step (d), comprises an auxin.

14. The method according to claim 13, wherein said auxin is phenylacetic acid.

15. The method according to claim 1, wherein said induction medium, in step (d), comprises glutamine at a level of from about 500 to about 1000 mg/L.

16. The method according to claim 1, wherein said induction medium, in step (d), additionally comprises ovary co-culture.

17. The method of claim 16, wherein the microspore containing plant segment, in step (a), is obtained from wheat.

18. A method of plant regeneration from microspores comprising the steps of:
  (a) harvesting a microspore-containing plant segment from a donor plant;
  (b) incubating said segment under pre-treatment conditions in absence of colchicine, and at a temperature from about 3° C. to about 6° C., to maintain from about 50% to about 100% of microspores at a uninucleate stage of development;
  (c) isolating microspores from said segment;
  (d) incubating said isolated microspores in an induction medium comprising an auxin and an arabinogalactan protein, to induce the production of embryos;
  (e) incubating said embryos in a differentiation medium to produce differentiated embryos; and
  (f) regenerating plants from said differentiated embryos.

19. The method of plant regeneration according to claim 18, wherein step (d) comprises placing embryos on a support.

20. The method according to claim 19, wherein said support comprises filter paper.

21. The method according to claim 18, wherein step (c) comprises blending or vortexing said segment in an aqueous solution of about 0.2 mol/liter to about 1.0 mol/liter sugar alcohol.

22. A method of producing a composition of microspores comprising:
  (a) harvesting a microspore-containing plant segment from a donor plant;
  (b) incubating said segment under pre-treatment conditions in absence of colchicine, and at a temperature from about 3° C. to about 6° C., to maintain from about 50% to about 100% of microspores at a uninucleate cell cycle;
  (c) isolating microspores from said segment; and
  (d) incubating said isolated microspores in an induction medium comprising an arabinogalactan protein to produce said composition of microspores comprising greater than about 25% viable microspores after a 10 day incubation period.

23. A method of producing a composition of microspores comprising:
  (a) harvesting a microspore-containing plant segment from a donor plant;
  (b) incubating said segment under pre-treatment conditions in absence of colchicine, and at a temperature from about 3° C. to about 6° C., to maintain from about 50% to about 100% of microspores at a uninucleate cell cycle;
  (c) isolating microspores from said segment; and
  (d) incubating said isolated microspores in an induction medium comprising an arabinogalactan protein to produce said composition of microspores comprising greater than about 15%.

24. A method of producing an embryo comprising the steps of:
  (a) harvesting a microspore-containing plant segment from a donor wheat or barley plant;
  (b) incubating said segment under pre-treatment conditions in absence of colchicine, and at a temperature from about 3° C. to about 6° C., to maintain from about 50% to about 100% of microspores at a uninucleate stage of development;
  (c) isolating microspores from said segment; and
  (d) incubating said isolated microspores in an induction medium comprising arabinogalactan protein to induce embryogenesis, thereby producing embryos.

25. A method of introducing a gene of interest into a microspore comprising, introducing a genetic construct comprising said gene of interest into said microspore, said microspore obtained following the steps of pre-treatment (step (b)) and isolation (step (c)) as defined in claim 1.

26. The method of claim 25, wherein the step of introducing comprises particle bombardment.

27. The method of claim 25, wherein the step of introducing comprises Agrobacterium mediated transformation.

* * * * *